United States Patent [19]
Gewirtz et al.

[11] Patent Number: 5,989,849
[45] Date of Patent: *Nov. 23, 1999

[54] ANTISENSE OF OLIGONUCLEOTIDES TO C-KIT PROTO-ONCOGENE AND IN VITRO METHODS

[75] Inventors: Alan M. Gewirtz; Bruno Calabretta, both of Philadelphia, Pa.

[73] Assignee: Temple University of the Commonwealth System of Higher Education, Philadephia, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/461,286

[22] Filed: Jun. 5, 1995

Related U.S. Application Data

[63] Continuation of application No. 08/129,123, Oct. 7, 1993, abandoned, which is a continuation-in-part of application No. 07/682,812, Apr. 9, 1991, abandoned.

[51] Int. Cl.$^6$ .............. C12Q 1/02; C12Q 1/68; C12N 5/00; A61K 48/00
[52] U.S. Cl. ................. 435/29; 435/5; 435/325; 435/372; 536/24.5; 514/44
[58] Field of Search ............ 536/24.5; 514/44, 514/908; 435/29, 6, 325, 372

[56] References Cited

U.S. PATENT DOCUMENTS 5,087,617  2/1992  Smith .

FOREIGN PATENT DOCUMENTS

WO92/22303  12/1992  WIPO .
WO93/09789  5/1993  WIPO .

OTHER PUBLICATIONS

Stein et al (1993) Science 261, 1004–1012.
Weiss (1991) Science News 139–108–109.
Tseng et al (1994) Cancer Gene Therapy 1, 65–71.
James (1991) Antiviral Chem. Chemother. 2, 191–214.
Cleary et al (1998) Cell 47, 19–28.
Linnenbach et al (1988) Proced. Nat. Acad. Sci. 85, 74–78.
Strohmeyer et (1991) Canc. Res. 51, 1811–1816.
Slamm et al (1989) Science 244, 707–712.
Majello et al (1986) Proced. Natl. Acad. Sci. 83, 9636–9640.
McGrath et al (1983) Nature 304, 901–904.
Caracciolo et al (1989) Science 245, 1107–1110.
Yarden et al (1987) EMBOJ 6, 3341–3351.
Orr–Urtregiv et al (1990) Develop. 109, 911–923.
Ratajczak et al (1992) Proced. Natl. Acad. Sci: 89, 11823–11827.
Ratajczak et al (1992) Blood 79, 1956–1961.
Smith et al (1986) Aust. NZ J. Med. 16, 39–42.
Park et al (1980) Blood 55, 595–601.
Gustavsson et al (1984) Canc. Res. 44, 4648–4652.
Veerman et al (1990) Brit. J. Hematology 74, 381–384.

*Primary Examiner*—Deborah Crouch
*Attorney, Agent, or Firm*—Seidel Gonda, Lavorgna & Monaco, PC

[57] ABSTRACT

Oligonucleotides are provided having a nucleotide sequence complementary to at least a portion of the mRNA transcript of the human c-<u>kit</u> gene. These "antisense" oligonucleotides are hybridizable to the c-<u>kit</u> mRNA transcript. Such oligonucleotides are useful in selectively inhibiting proliferation of erythroid cells, particularly in disorders characterized by an elevated hematocrit due to over-production of erythrocytes. The antisense oligomers also have activity agent hematologic neoplastic cells and are therefore suitable as bone marrow purging agents.

7 Claims, 1 Drawing Sheet

FIG. 3

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 40 Nucleotides

```
         (B) TYPE:         nucleic acid
         (C) STRANDEDNESS: single stranded
         (D) TOPOLOGY:     linear (xi) SEQUENCE DESCRIPTION: SEQ ID NO:1:

GAACGCAGAG AAAATCCCAG GCGCCGCGAG CGCCTCTCAT                              40

(2) INFORMATION FOR SEQ ID NO:2:

(i) SEQUENCE CHARACTERISTICS:
         (A) LENGTH:       26 Nucleotides
         (B) TYPE:         nucleic acid
         (C) STRANDEDNESS: single stranded
         (D) TOPOLOGY:     linear (xi) SEQUENCE DESCRIPTION: SEQ ID NO:2:

TCCCAGGCGC CGCGAGCGCC TCTCAT                                             26

(2) INFORMATION FOR SEQ ID NO:3:

(i) SEQUENCE CHARACTERISTICS:
         (A) LENGTH:       25 Nucleotides
         (B) TYPE:         nucleic acid
         (C) STRANDEDNESS: single stranded
         (D) TOPOLOGY:     linear (xi) SEQUENCE DESCRIPTION: SEQ ID NO:3:

CCCAGGCGCC CGCAGCGCCT CTCAT                                              25

(2) INFORMATION FOR SEQ ID NO:4:

(i) SEQUENCE CHARACTERISTICS:
         (A) LENGTH:       24 Nucleotides
         (B) TYPE:         nucleic acid
         (C) STRANDEDNESS: single stranded
         (D) TOPOLOGY:     linear (xi) SEQUENCE DESCRIPTION: SEQ ID NO:4:

CCAGGCGCCG CGAGCGCCTC TCAT                                               24

(2) INFORMATION FOR SEQ ID NO:5:

(i) SEQUENCE CHARACTERISTICS:
         (A) LENGTH:       23 Nucleotides
         (B) TYPE:         nucleic acid
         (C) STRANDEDNESS: single stranded
         (D) TOPOLOGY:     linear (xi) SEQUENCE DESCRIPTION: SEQ ID NO:5:

CAGGCGCCGC GAGCGCCTCT CAT                                                23

(2) INFORMATION FOR SEQ ID NO:6:

(i) SEQUENCE CHARACTERISTICS:
         (A) LENGTH:       22 Nucleotides
         (B) TYPE:         nucleic acid
         (C) STRANDEDNESS: single stranded
         (D) TOPOLOGY:     linear (xi) SEQUENCE DESCRIPTION: SEQ ID NO:6:

AGGCGCCGCG AGCGCCTCTC AT                                                 22

(2) INFORMATION FOR SEQ ID NO:7:

(i) SEQUENCE CHARACTERISTICS:
         (A) LENGTH:       21 Nucleotides
         (B) TYPE:         nucleic acid
         (C) STRANDEDNESS: single stranded
```

(D) TOPOLOGY:  linear (xi) SEQUENCE DESCRIPTION: SEQ ID NO:7:

GGCGCCGCGA GCGCCTCTCA T                                             21

(2) INFORMATION FOR SEQ ID NO:8:

(i) SEQUENCE CHARACTERISTICS:
            (A) LENGTH:  20 Nucleotides
            (B) TYPE:    nucleic acid
            (C) STRANDEDNESS:  single stranded
            (D) TOPOLOGY:  linear (xi) SEQUENCE DESCRIPTION: SEQ ID NO:8:

GCGCCGCGAG CGCCTCTCAT                                               20

(2) INFORMATION FOR SEQ ID NO:9:

(i) SEQUENCE CHARACTERISTICS:
            (A) LENGTH:  19 Nucleotides
            (B) TYPE:    nucleic acid
            (C) STRANDEDNESS:  single stranded
            (D) TOPOLOGY:  linear (xi) SEQUENCE DESCRIPTION: SEQ ID NO:9:

CGCCGCGAGC GCCTCTCAT                                                19

(2) INFORMATION FOR SEQ ID NO:10:

(i) SEQUENCE CHARACTERISTICS:
            (A) LENGTH:  18 Nucleotides
            (B) TYPE:    nucleic acid
            (C) STRANDEDNESS:  single stranded
            (D) TOPOLOGY:  linear (xi) SEQUENCE DESCRIPTION: SEQ ID NO:10:

GCCGCGAGCG CCTCTCAT                                                 18

(2) INFORMATION FOR SEQ ID NO:11:

(i) SEQUENCE CHARACTERISTICS:
            (A) LENGTH:  17 Nucleotides
            (B) TYPE:    nucleic acid
            (C) STRANDEDNESS:  single stranded
            (D) TOPOLOGY:  linear (xi) SEQUENCE DESCRIPTION: SEQ ID NO:11:

CCGCGAGCGC CTCTCAT                                                  17

(2) INFORMATION FOR SEQ ID NO:12:

(i) SEQUENCE CHARACTERISTICS:
            (A) LENGTH:  16 Nucleotides
            (B) TYPE:    nucleic acid
            (C) STRANDEDNESS:  single stranded
            (D) TOPOLOGY:  linear (xi) SEQUENCE DESCRIPTION: SEQ ID NO:12:

CGCGAGCGCC TCTCAT                                                   16

(2) INFORMATION FOR SEQ ID NO:13:

(i) SEQUENCE CHARACTERISTICS:
            (A) LENGTH:  15 Nucleotides
            (B) TYPE:    nucleic acid
            (C) STRANDEDNESS:  single stranded
            (D) TOPOLOGY:  linear (xi) SEQUENCE DESCRIPTION: SEQ ID NO:13:

GCGAGCGCCT CTCAT                                                                       15

(2) INFORMATION FOR SEQ ID NO:14:

(i) SEQUENCE CHARACTERISTICS:
        (A) LENGTH:  18 Nucleotides
        (B) TYPE:    nucleic acid
        (C) STRANDEDNESS: single stranded
        (D) TOPOLOGY: linear (xi) SEQUENCE DESCRIPTION: SEQ ID NO:14:

ATGAGAGGCG CTCGCGGC                                                                    18

(2) INFORMATION FOR SEQ ID NO:15:

(i) SEQUENCE CHARACTERISTICS:
        (A) LENGTH:  18 Nucleotides
        (B) TYPE:    nucleic acid
        (C) STRANDEDNESS: single stranded
        (D) TOPOLOGY: linear (xi) SEQUENCE DESCRIPTION: SEQ ID NO:15:

GCACCGTCTG CCAGTCGC                                                                    18

(2) INFORMATION FOR SEQ ID NO:16:

(i) SEQUENCE CHARACTERISTICS:
        (A) LENGTH:  22 Nucleotides
        (B) TYPE:    nucleic acid
        (C) STRANDEDNESS: single stranded
        (D) TOPOLOGY: linear (xi) SEQUENCE DESCRIPTION: SEQ ID NO:16:

CTAGGAATGT GTAAGTGCCT CC                                                               22

(2) INFORMATION FOR SEQ ID NO:17:

(i) SEQUENCE CHARACTERISTICS:
        (A) LENGTH:  22 Nucleotides
        (B) TYPE:    nucleic acid
        (C) STRANDEDNESS: single stranded
        (D) TOPOLOGY: linear (xi) SEQUENCE DESCRIPTION: SEQ ID NO:17:

GGTTGACTAT CAGTTCAGCG AG 22

(2) INFORMATION FOR SEQ ID NO:18:

(i) SEQUENCE CHARACTERISTICS:
        (A) LENGTH:  21 Nucleotides
        (B) TYPE:    nucleic acid
        (C) STRANDEDNESS: single stranded
        (D) TOPOLOGY: linear (xi) SEQUENCE DESCRIPTION: SEQ ID NO:18:

GATCCACTGC TGGTGTTCAG G                                                                21

ANTISENSE OF OLIGONUCLEOTIDES TO C-KIT PROTO-ONCOGENE AND IN VITRO METHODS

This is a continuation of copending application Ser. No. 08/129,123, filed Oct. 7, 1993, now abandoned, which is a continuation-in-part of copending application Ser. No. 07/682,812, filed May 9, 1991, now abandoned.

FIELD OF THE INVENTION

The invention relates to antisense oligonucleotides to proto-oncogenes, in particular to antisense oligonucleotides to the c-kit gene, and the use of such oligonucleotides to selectively inhibit proliferation of certain cells.

Reference to Government Grant

The invention described herein was supported in part by National Institutes of Health grants CA36896 and CA01324. The United States government has certain rights in the invention.

BACKGROUND OF THE INVENTION

The c-kit gene is the normal homologue of v-kit, the HZ4 feline sarcoma virus oncogene. It resides on human chromosome 4. The gene encodes a dimeric transmembrane glycoprotein receptor with tyrosine kinase activity that appears to be highly related to the receptors for colony stimulating factor-1 and platelet derived growth factor. (Yarden et. al., *The EMBO Journal*, 6, 3341–3351 (1987)). Like these receptors, c-kit also appears to belong to the immunoglobulin gene superfamily.

The mouse c-kit gene has been mapped to chromosome 5 where it was determined to be allelic with the dominant white spotting locus (W) (Chabot et al., *Nature* 335, 88–89 (1988). C-kit mutations are commonly found in W mice and, in addition to abnormalities affecting coat color and gonadal development, they also have a variety of hematopoietic defects. Macrocytic anemia is one of the most striking and profound of these abnormalities. The $W^{42}$ mutation, associated with a particularly severe hematologic manifestation, has been shown to be due to a missense mutation leading to replacement of one amino acid and defective tyrosine kinase activity (Tan et al., *Science* 247, 209 (1990)). Such animals are also known to have about one-third of the erythroid burst forming units of healthy wild-type littermates (Goldwather et al., *Exp. Heme.* 18, 936 (1990)).

The ligand for the c-kit receptor has now been identified, molecularly cloned and expressed (Yarden et. al., *The EMBO Journal*, 6, 3341–3351 (1987)). The encoded protein, known as stem cell factor (SCF), mast cell growth factor (MGF), or steel factor (SLF) is the product of a gene which resides at the steel (S1) locus. Mice with S1 mutations have phenotypic abnormalities quite similar to those of W mice. The W mouse lacks, or has defects in, a critical signal transducing receptor encoded by c-kit. The S1 mouse has defects in the ligand which stimulates the receptor.

The importance of the c-kit ligand-receptor system in human hematopoiesis is unclear. No human mutations at the corresponding locii have been described. Studies in mice may have very limited applicability to human systems. Moreover, even if a tissue is shown to express a particular message, the importance of the message to expression of a cellular phenotype is not known until the cell is deprived of the encoded protein. Biological systems are redundant. Lack of a protein can often be compensated by another protein of the same family. It is therefore not predictable that inhibition of expression of a particular gene will result in altered phenotype.

SUMMARY OF THE INVENTION

Antisense oligonucleotides and pharmaceutical compositions thereof with pharmaceutical carriers are provided. Each oligonucleotide has a nucleotide sequence complementary to at least a portion of the mRNA transcript of the human c-kit gene. The oligonucleotide is hybridizable to the mRNA transcript. Preferably, the oligonucleotide is at least a 12-mer oligonucleotide, that is, an oligomer containing at least 12 nucleotide residues. In particular, the oligomer is advantageously a 12-mer to a 40-mer, preferably an oligodeoxynucleotide. While oligonucleotides smaller than 12-mers may be utilized, they are statistically more likely to hybridize with non-targeted sequences, and for this reason may be less specific. In addition, a single mismatch may destabilize the hybrid. While oligonucleotides larger than 40-mers may be utilized, uptake may be more difficult. Moreover, partial matching of long sequences may lead to non-specific hybridization, and non-specific effects. Preferably, the oligonucleotide is a 15- to 30-mer oligodeoxynucleotide, more advantageously an 18- to 26-mer. A 15- to 21-mer is most preferred.

While in principle oligonucleotides having a sequence complementary to any region of the c-kit gene find utility in the present invention, oligonucleotides complementary to a portion of the c-kit mRNA transcript including the translation initiation codon are particularly preferred. Also preferred are oligonucleotides complementary to a portion of the c-kit mRNA transcript lying within about 40 nucleotides upstream (the 5' direction) or about 40 nucleotides downstream (the 3' direction) from the translation initiation codon.

The invention also provides a method for inhibiting proliferation of erythroid cells comprising administering to a host in need of such treatment an effective amount of the c-kit antisense oligonucleotides of the invention.

The invention provides a method for treating hematologic neoplasms characterized by c-kit expression comprising administering an effective amount of c-kit antisense oligonucleotide in vivo or ex vivo to a host in need of such treatment, or to cells harvested from the host.

Administration of the c-kit oligonucleotides is also useful in treatment of malignant melanoma, and testicular or ovarian tumors.

As used in the herein specification and appended claims, unless otherwise indicated, the term "oligonucleotide" includes both oligomers of ribonucleotide i.e., oligoribonucleotides, and oligomers of deoxyribonucleotide i.e., oligodeoxyribonucleotides (also referred to herein as "oligodeoxynucleotides"). Oligodeoxynucleotides are preferred.

As used herein, unless otherwise indicated, the term "zoligonucleotide" also includes oligomers which may be large enough to be termed "polynucleotides".

The terms "oligonucleotide" and "oligodeoxynucleotide" include not only oligomers and polymers of the biologically significant nucleotides, i.e. nucleotides of adenine ("A"), deoxyadenine ("dA"), guanine ("G"), deoxyguanine ("dG"), cytosine ("C"), deoxycytosine ("dC")), thymine ("T") and uracil ("U"), but also oligomers and polymers hybridizable to the c-kit mRNA transcript which may contain other nucleotides. Likewise, the terms "oligonucleotide" and "oligodeoxynucleotidel" include oligomers and polymers wherein one or more purine or pyrimidine moieties, sugar moieties or internucleotide linkages is chemically modified. The term "oligonucleotide" is thus understood to also include oligomers which may properly be designated as "oligonucleosides" because of modification of the internucleotide phosphodiester bond. Such modified oligonucleotides include, for example, the alkylphosphonate oligonucleosides, discussed below.

The term "phosphorothioate oligonucleotide" means an oligonucleotide wherein one or more of the internucleotide linkages is a phosphorothioate group, as opposed to the phosphodiester group which is characteristic of unmodified oligonucleotides.

By "alkylphosphonate oligonucleoside" is meant an oligonucleotide wherein one or more of the internucleotide linkages is an alkylphosphonate group, wherein R is an alkyl group, preferably methyl or ethyl.

The term "downstream" when used in reference to a direction along a nucleotide sequence means the 5'→3' direction. Similarly, the term "upstream" means the 3'→5' direction.

The term "c-kit mRNA transcript" means the presently known mRNA transcript of the human c-kit gene, or any further transcripts which may be elucidated.

DETAILED DESCRIPTION OF THE INVENTION

We have discovered that the c-kit gene is of predominant importance in human erythropoiesis. We have found that the protein which this gene expresses, a receptor for tyrosine kinase, transduces a signal which acts in concert with interleukin-3 (IL-3) to optimize cell proliferation, particularly erythroid burst forming units (BFU-E).

The putative DNA sequence complementary to the MRNA transcript of the human c-kit gene has been reported by Yarden et al., *The EMBO Journal*, 6, 3341–3351 (1987), the entire disclosure of which is incorporated herein by reference. The nucleotide sequence and predicted amino acid sequence are set forth in FIG. 3 thereof. The c-kit polypeptide is synthesized by translation of a single 5-kb MRNA, which contains an open reading frame coding for a 976 amino acid polypeptide.

The antisense oligonucleotides of the invention may be synthesized by any of the known chemical oligonucleotide synthesis methods. Such methods are generally described, for example, in Winnacker, *From Genes to Clones: Introduction to Gene Technology*, VCH Verlagsgesellschaft mbH (H. Ibelgaufts trans. 1987).

Any of the known methods of oligonucleotide synthesis may be utilized in preparing the instant antisense oligonucleotides.

The antisense oligonucleotides are most advantageously prepared by utilizing any of the commercially available, automated nucleic acid synthesizers, for example, the Applied Biosystems 380B DNA Synthesizer, which utilizes β-cyanoethyl phosphoramidite chemistry.

Since the complete nucleotide synthesis of DNA complementary to the c-kit mRNA transcript is known, antisense oligonucleotides hybridizable with any portion of the mRNA transcript may be prepared by the oligonucleotide synthesis methods known to those skilled in the art.

While any length oligonucleotide may be utilized in the practice of the invention, sequences shorter than 12 nucleotides may be less specific in hybridizing to the target c-kit mRNA, may be more easily destroyed by enzymatic digestion, and may be destabilized by even a single base pair mismatch. Hence, oligonucleotides having 12 or more nucleotides are preferred.

Long sequences, particularly sequences longer than about 40 nucleotides, may be somewhat less effective in inhibiting c-kit translation because of decreased uptake by the target cell. Thus, oligomers of 12–40 nucleotides are preferred, more preferably 15–30 nucleotides, most preferably 18–26 nucleotides. Sequences of 18–21 nucleotides are particularly preferred. While sequences of 18–21 nucleotides are most particularly preferred, for unmodified oligonucleotides, slightly longer chains of up to about 26 nucleotides, are preferred for modified oligonucleotides such as phosphorothioate oligonucleotides, which hybridize less strongly to mRNA than unmodified oligonucleotides. oligonucleotides complementary to and hybridizable with any portion of the c-kit mRNA transcript are, in principle, effective for inhibiting translation of the transcript, and capable of inducing the effects herein described. It is believed that translation is most effectively inhibited by blocking the mRNA at a site at or near the initiation codon. Thus, oligonucleotides complementary to the 5'-terminal region of the c-kit MRNA transcript are preferred. The oligonucleotide is preferably directed to a site at or near the initiation codon for protein synthesis. The following 40-mer oligodeoxynucleotide is complementary to the c-kit mRNA transcript beginning with the initiation codon of the transcript and extending downstream (in the 5' direction): GAAC'(CAGAG AAAATPC-CCAG GCGCCGCGAG CGCCTCTCAT (SEQ ID NO:1).

Smaller oligomers based upon the above sequence, in particular oligomers hybridizable to segments of the c-kit message containing the initian codon, may be utilized. Particularly preferred are the following 15- to 26-mers:

(SEQ ID NO:2)
(SEQ ID NO:3)
(SEQ ID NO:4)
(SEQ ID NO:5)
(SEQ ID NO:6)
(SEQ ID NO:7)
(SEQ ID NO:8)
(SEQ ID NO:9)
(SEQ ID NO:10)
(SEQ ID NO:11)
(SEQ ID NO:12)
(SEQ ID NO:13)

Oligonucleotides hybridizable to the c-kit mRNA transcript finding utility according to the present invention include not only native oligomers of the biologically significant nucleotides, i.e., A, d, G., dG, C, dC, T and U, but also oligonucleotide species which have been modified for improved stability and/or lipid solubility. The oligonucleotides may be any of a number of types, including those having a charged or uncharged backbone. For example, it is known that enhanced lipid solubility and/or resistance to nuclease digestion results by substituting an alkyl group or sulfur atom for a phosphate oxygen in the internucleotide phosphodiester linkage to form alkylphosphonate oligonucleotide or phosphorothioate oligonucleotides. The phosphorothioates, in particular, are stable to nuclease cleavage and soluble in lipid. They may be synthesized by known automatic synthesis methods.

The oligonucleotide employed may represent an unmodified oligonucleotide or an oligonucleotide analog. One group of such analogs, the alkyl phosphonates, includes but is not limited to the ethyl or methyl phosphonate analogs disclosed by U.S. Pat. No. 4,469,863.

Non-ionic oligonucleotides are characterized by increased resistance to nuclease hydrolysis and/or increased cellular uptake, while retaining the ability to form stable complexes with complementary nucleic acid sequences. The alkylphosphonates in particular, are stable to nuclease cleavage and soluble in lipid. The preparation of alkylphosphonate oligonucleosides is disclosed in U.S. Pat. No. 4,469,863.

Methylphosphonate oligomers can be prepared by a variety of methods, both in solution and on insoluble polymer supports (Agrawal and Riftina, Nucl. Acids Res., 6, 3009–3024 (1979); Miller et al., Biochemistry, 18, 5134–5142 (1979), Miller et al., J. Biol. Chem., 255, 9659–9665 (1980); Miller et al., Nucl. Acids Res., 11, 5189–5204 (1983), Miller et al., Nucl. Acids Res., 11, 6225–6242 (1983), Miller et al., Biochemistry, 25, 5092–5097 (1986); Engels and Jager, Angew. Chem. Suppl. 912 (1982); Sinha et al., Tetrahedron Lett. 24, 877–880 (1983); Dorman et al, Tetrahedron, 40, 95–102 (1984); Jager and Engels, Tetrahedron Lett., 25, 1437–1440 (1984); Noble et al., Nucl. Acids Res., 12, 3387–3404 (1984); Callahan et al., Proc. Natl. Acad. Sci. USA, 83, 1617–1621 (1986); Koziolkiewicz et al., Chemica Scripta, 26, 251–260 (1986); Agrawal and Goodchild, Tetrahedron Lett., 38, 3539–3542 (1987); Lesnikowski et al., Tetrahedron Lett., 28, 5535–5538 (1987); Sarin et al., Proc. Natl. Acad. Sci. USA, 85, 7448–7451 (1988)).

The most efficient procedure for preparation of methylphosphonate oligonucleosides involves use of 5'O-dimethoxytrityldeoxynucleoside-3'-O-diisopropylmethylphosphoramidite intermediates, which are similar to the methoxy or β-cyanoethyl phosphoramidite reagents used to prepare oligodeoxyribonucleotides. The methyl-phosphonate oligomers can be prepared on controlled pore glass polymer supports using anautomated DNA synthesizer (Sarin et al., Proc. Natl. Acad. Sci. USA, 85, 7448–7451 (1988)).

Resistance to nuclease digestion may also be achieved by modifying the internucleotide linkage at both the 5' and 3' termini with phosphoroamidites according to the procedure of Dagle et al., Nucl. Acids Res. 18, 4751–4757 (1990).

Phosphorothioate oligonucleotides contain a sulfur-for-oxygen substitution in the internucleotide phosphodiester bond. Phosphorothioate oligonucleotides combine the properties of effective hybridization for duplex formation with substantial nuclease resistance, while retaining the water solubility of a charged phosphate analogue. The charge is believed to confer the property of cellular uptake via a receptor (Loke et al., Proc. Natl. Acad. Sci. U.S.A. 86, 3474–3478 (1989)).

Phosphorothioate oligodeoxynucleotide are described by LaPlanche, et al., Nucleic Acids Research 14, 9081 (1986) and by Stec et al., J. Am. Chem. Soc. 106, 6077 (1984). The general synthetic method for phosphorothioate oligonucleotides was modified by Stein et al., Nucl. Acids Res., 16, 3209–3221 (1988), so that these compounds may readily be synthesized on an automatic synthesizer using the phosphoramidite approach.

Furthermore, recent advances in the production of oligoribonucleotide analogues mean that other agents may also be used for the purposes described here, e.g., 2'-O-methylribonucleotides (Inoue et al., Nucleic Acids Res. 15, 6131 (1987) and chimeric oligonucleotides that are composite RNA-DNA analogues (Inoue et al., FEBS Lett. 215, 327 (1987).

While inhibition of c-kit MRNA translation is possible utilizing either antisense oligoribonucleotides or oligodeoxyribonucleotides, free oligoribonucleotides are more susceptible to enzymatic attack by ribonucleases than oligodeoxyribonucleotides. Hence, oligodeoxyribonucleotides are preferred in the practice of the present invention. Oligodeoxyribonucleotides are further preferred because, upon hybridization with c-kit mRNA, the resulting DNA-RNA hybrid duplex is a substrate for RNase H, which specifically attacks the RNA portion of DNA-RNA hybrid. Degradation of the mRNA strand of the duplex releases the antisense oligodeoxynucleotide for hybridization with additional c-kit messages.

In general, the antisense oligonucleotides of the present invention will have a sequence which is completely complementary to the target portion of the c-kit message. Absolute complementarity is not however required, particularly in larger oligomers. Thus, reference herein to a "nucleotide sequence complementary to at least a portion of the mRNA transcript" of c-kit does not necessarily mean a sequence having 100% complementarity with the transcript. In general, any oligonucleotide having sufficient complementarity to form a stable duplex with c-kit mRNA, that is, an oligonucleotide which is "thybridizable", is suitable. Stable duplex formation depends on the sequence and length of the hybridizing oligonucleotide and the degree of complementarity with the target region of the c-kit message. Generally, the larger the hybridizing oligomer, the more mismatches may be tolerated. More than one mismatch probably will not be tolerated for antisense oligomers of less than about 21 nucleotides. One skilled in the art may readily determine the degree of mismatching which may be tolerated between any given antisense oligomer and the target c-kit message sequence, based upon the melting point, and therefore the stability of the resulting duplex. Melting points of duplexes of a given base pair composition can be determined from standard texts, such as *Molecular Cloning: A Laboratory Manual,* (2nd edition, 1989), J. Sambrook et al., eds.

While oligonucleotides capable of stable hybridization with any region of the c-kit message are within the scope of the present invention, oligonucleotides complementary to a region including the initiation codon are believed particularly effective. Particularly preferred are oligonucleotides hybridizable to a region of the c-kit mRNA up to 40 nucleotides upstream (in the 5' direction) of the initiation codon or up to 40 nucleotides downstream (in the 3' direction) of that codon.

The antisense oligonucleotides of the invention inhibit human erythropoiesis, as indicated by inhibition of colony forming unit-erythroid cells (CFU-E) and burst forming unit-erythroyd cells (BFU-E). However, they do not appear to inhibit proliferation of cells of other lineages, such as colony forming unit-granulocyte-macrophage cells (CFU-GM) and colony forming unit-megakaryocyte cells (CFU-MEG). CFU-GM cells and CFU-MEG cells are the progenitors of blood granulo- cytes and platelets, respectively. This pharmaceutically significant differential sensitivity makes the instant oligonucleotides useful in treating disorders characterized by elevated production of red blood cells.

The antisense oligonucleotides of the invention are believed useful in the treatment of any one of a variety of conditions characterized by an elevated hematocrit due to overproduction of erythrocytes. One such disorder, polycythemia, may arise from a variety of causes and is classified as either relative, secondary or primary polycythemia.

In relative polycythemia, the red cell mass is normal. Plasma volume is decreased. The increase in erythrocytes is therefore a concentration effect. Rplative polycythemia is associated with diabetic acidosis, diarrhea, or diabetes insipidus. It is also associated with the intake of diuretics.

In secondary polycythemia, red cell mass is increased secondarily to elevated erythropoietin (EPO) production. This occurs in individuals who have located to higher altitudes, since decreased oxygen simulates anemia, which is a triggering signal for increase of erythrocyte production. Secondary polycythemia may also occur in patients who have significant pulmonary or cardiac disfunction. Decreased oxygen delivery to tissues simulates anemia which triggers a signal to increase erythrocyte production. Secondary polycythemia may also occur in individuals who have tumors which are capable of synthesizing EPO, as in hypernephroma, cerebellar hemangioma and uterine leiomyoma.

Primary polycythemia is characterized by an increase in red cell mass, with either normal or decreased EPO levels. Primary polycythemia occurs in the myeloproliferative disorders, in particular polycythemia vera (PV). Disorders such as PV are true stem cell disorders. Accordingly, the white blood cell count and platelet count may be elevated. However, control of erythrocyte production is the primary objective in management of PV. Control of PV is usually effected by phlebotomy in secondary causes (if treatment of the primary disease is ineffective), and by a combination of phlebotomy and chemotherapy. Chemotherapeutic treatment of PV typically utilizes alkylating agents such as busulfan, melphalan, cyclophosphamide, chlorambucil or radioactive phosphorous in the form of sodium phosphate-$^{32}$P.

The rapid fluid shifts imposed by phlebotomy in the treatment of PV can be dangerous for patients with cardiac/pulmonary disease. Phlebotomy is also associated with a significant risk of fatal thrombosis. (Burk et al., *Semin. Hematol.* 23, 132 (1986); Ellis et al., id. at 144). Control of erythrocyte production by administration of the c-kit antisense oligomers of the present invention is an attractive alternative to phlebotomy and chemotherapy.

The antisense oligonucleotides of the invention are further believed to possess utility in the treatment of hematologic malignancies. Hematologic neoplastic cells believed sensitive to the instant c-kit antisense oligonucleotides include, for example, myeloid leukemia cells. The appearance of these cells in the bone marrow and elsewhere in the body is associated with various disease conditions, such as all of the various French-American-British (FAB) subtypes of acute myeloid leukemia, and chronic myeloid leukemia.

The c-kit antisense oligonucleotides are believed particularly useful against acute myelogenous leukemia (AML). Significant activity against chronic myelogenous leukemia (CML) has also been demonstrated. CML, in particular, is characterized by abnormal proliferation of immature granulocytes—neutrophils, eosinophils, and basophils—in the blood, the bone marrow, the spleen, the liver, and sometimes other tissues. The essential feature is accumulation of granulocytic precursors in these tissues. The patient who presents symptoms will characteristically have more than 20,000 white blood cells per $\mu$l, and the count may exceed 400,000. Virtually all CML patients will develop "blast crisis", the terminal stage of the disease during which immature blast cells rapidly proliferate, leading to patient death.

Since c-kit function appears to be important for development of melanocytes, i.e., neural crest-derived pigment cells, and germ (gonadal) cells, it is believed that the antisense oligonucleotides of the present invention are useful for the treatment of malignant melanoma and testicular or ovarian tumors.

The antisense oligonucleotides of the invention find utility as bone marrow purging agents. They may be utilized in vitro to cleanse bone marrow contaminated by hematologic neoplasms. They are believed useful as purging agents in either allogeneic or autologous bone marrow transplantation. They are believed particularly effective in the treatment of hematological malignancies or other neoplasias which metastasize in the bone marrow.

According to a method for bone marrow purging, bone marrow is harvested from a donor by standard operating room procedures from the iliac bones of the donor. Methods of aspirating bone marrow from donors are well-known in the art. Examples of apparatus and processes for aspirating bone marrow from donors are disclosed in U.S. Pat. Nos. 4,481,946 and 4,486,188. Sufficient marrow is withdrawn so that the recipient, who is either the donor (autologous transplant) or another individual (allogeneic transplant), may receive from about $4\times10^8$ to about $8\times10^8$ processed marrow cells per kg of bodyweight. This generally requires aspiration of about 750 to about 1000 ml of marrow. The aspirated marrow is filtered until a single cell suspension, known to those skilled in the art as a "buffy coat" preparation, is obtained. This suspension of leukocytes is treated with c-kit antisense oligonucleotides in a suitable carrier, advantageously in a concentration of about 8 mg/ml. Alternatively, the leucocyte suspension may be stored in liquid nitrogen using standard procedures known to those skilled in the art until purging is carried out. The purged marrow can be stored frozen in liquid nitrogen until ready for use. Methods of freezing bone marrow and biological substances are disclosed, for example, in U.S. Pat. Nos. 4,107,937 and 4,117,881.

Other methods of preparing bone marrow for treatment with c-kit antisense may be utilized, which methods may result in even more purified preparations of hematopoietic cells than the aforesaid buffy coat preparation.

One or more hematopoietic growth factors may be added to the aspirated marrow or buffy coat preparation to stimulate growth of hematopoietic neoplasms, and thereby increase their sensitivity to the toxicity of the c-kit antisense oligonucleotides. Such hematopoietic growth factors include, for example, IL-3 and granulocyte macrophage colony stimulating factor (GM-CSF). The recombinant human versions of such growth factors are advantageously employed.

After treatment with the antisense oligonucleotides, the cells to be transferred are washed with autologous plasma or buffer to remove unincorporated oligomer. The washed cells are then infused back into the patient.

For in vivo use, the antisense oligonucleotides may be combined with a pharmaceutical carrier, such as a suitable liquid vehicle or excipient and an optional auxiliary additive or additives. The liquid vehicles and excipients are conventional and commercially available. Illustrative thereof are distilled water, physiological saline, aqueous solution of dextrose, and the like. For in vivo antineoplastic use and in vivo erythroid cell reduction, the c-kit mRNA antisense oligonucleotides are preferably administered parenterally, most preferably intravenously. The vehicle is designed accordingly. It is also possible to administer such compounds ex vivo by isolating lymphocytes from peripheral blood, treating them with the antisense oligonucleotides, then returning the treated lymphocytes to the peripheral blood of the donor. Ex vivo techniques have been utilized in treatment of cancer patients with interleukin-2 activated lymphocytes, and are well-known to those skilled in the art.

In addition to administration with conventional carriers, the antisense oligonucleotides may be administered by a variety of specialized oligonucleotide delivery techniques. For example, oligonucleotides may be encapsulated in liposomes for therapeutic delivery. The oligonucleotide, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, ionic surfactants such as diacetylphosphate, stearylamine, or phosphatidic acid, and/or other materials of a hydrophobic nature. Oligonucleotides have been successfully encapsulated in unilameller liposomes.

Reconstituted Sendai virus envelopes have been successfully used to deliver RNA and DNA to cells. Arad et al., *Biochem. Biophy. Acta.* 859, 88–94 (1986).

The oligonucleotides may be conjugated to poly(L-lysine) to increase cell penetration. Such conjugates are described by Lemaitre et al., *Proc. Natl. Acad. Sci. USA*, 84, 648–652 (1987). The procedure requires that the 3'-terminal nucleotide be a ribonucleotide. The resulting aldehyde groups are then randomly coupled to the epsilon-amino groups of lysine residues of poly(L-lysine) by Schiff base formation, and then reduced with sodium cyanoborohydride. This procedure converts the 3'-terminal ribose ring into a morpholine structure antisense oligomers.

For ex vivo antineoplastic application, such as, for example, in bone marrow purging, the c-kit antisense oligonucleotides may be administered in amounts effective to kill neoplastic cells while maintaining the viability of normal hematologic cells. Such amounts may vary depending on the nature and extent of the neoplasm, the particular oligonucleotide utilized, the relative sensitivity of the neoplasm to the oligonucleotide, and other factors. Concentrations from about 10 to 200 $\mu$g/ml per $10^5$ cells may be employed, preferably from about 40 to 150 $\mu$g/ml per $10^5$ cells. Supplemental dosing of the same or lesser amounts of oligonucleotide are advantageous to optimize the treatment. Thus, for purging bone marrow containing $2\times10^7$ cell per ml of marrow volume, dosages of from about 2 to 40 mg antisense per ml of marrow may be effectively utilized, preferably from about 8 to 24 mg/ml. Greater or lesser amounts of oligonucleotide may be employed.

For in vivo use, the c-kit antisense oligonucleotides may be administered in an amount sufficient to result in extracellular concentrations approximating the above stated in vitro concentrations. Preferably, the intracellular concentration is in the range of from about 10 to about 100 $\mu$g/ml. The actual dosage administered may take into account the size and weight of the patient, whether the nature of the treatment is prophylactic or therapeutic in nature, the age, weight, health and sex of the patient, the route of administration, and other factors. Those skilled in the art should be readily able to derive suitable dosages and schedules of administration to suit the specific circumstance. The daily dosage may range from about 0.1 to 1,000 mg oligonucleotide per day, preferably from about 10 to about 1,000 mg per day. Greater or lesser amounts of oligonucleotide may be administered, as required. Those skilled in the art should be readily able to derive appropriate dosages and schedules of administration to suit the specific circumstances and needs of the patient.

The present invention is described in greater detail in the following non-limiting examples.

EXAMPLE 1

Effect of c-kit Antisense Oligomer Exposure on Normal

Hematopoietic Progenitor Cell Growth.

The effect of c-kit antisense oligonucleotide on hematopoietic progenitor cell cloning efficiency and development was systematically investigated by assessing CFU-E, burst-forming unit-erythroid (BFU-E), CFU-GM, and CFU-MEG growth after oligomer exposure.

Cells: Human bone marrow cells (BMC) were obtained from normal, healthy volunteers by Ficoll-Hypaque density gradient centrifugation, and were partially enriched for hematopoietic progenitors by removal of adherent, phagocytic elements and T lymphocytes (Gewirtz et al., *J. Immunol.* 139, 2915–2925 (1987)). For some experiments, the adherent, T lymphocyte-de-pleted population (A"T"MNC) was further enriched by positively selecting CD34+cells with immunomagnetic beads (Dynal A.S., Oslo, Norway). The A"T"MNC cells were suspended in supplemented alpha medium and incubated with mouse anti-HPCA-I antibody in 1:20 dilution, 45 minutes, at 4° C. with gentle inverting of tubes. Cells were washed×3 in Supplemented alpha medium, and then incubated with beads coated with the Fc fragment of goat anti-mouse IgG$_1$ (75 μl of immunobeads/10$^7$ A"T"MNC). After 45 minutes of incubation (4° C.), cells adherent to the beads were positively selected using a magnetic particle concentrator as directed by the manufacturer.

Oligodeoxynucleotides: Unmodified, 18-nucleotide oligodeoxynucleotides (oligomers) were synthesized as previously reported (Gewirtz et al., Science 242, 1303–1306 (1988)). In brief, oligomers were synthesized on an Applied Biosystems 380B DNA synthesizer by means of a β-cyanoethyl phosphoramidite chemistry. Oligomers were purified by ethanol precipitation and multiple washes in 70% ethanol. They were then lyophilized to dryness and redissolved in culture medium prior to use at a concentration of 1 μg/μl (0.175 μM). Oligomer sequences employed, corresponding to codons 1–6' of the published human c-kit cDNA sequence (Yarden, et al., The EMBO Journal 6, 3341–3351 (1987)), were as follows: ATGAGAGGCG CTCGCGGC (SEQ ID NO:14), sense oligomer; GCCGCGAGCG CCTCTCAT (SEQ ID NO:10), antisense oligomer; and GCACCGTCTG CCAGTCGC (SEQ ID NO:15), scrambled sequence oligomer.

Oligomer Treatment of Cells: Cells were exposed to oligomers as previously described (Gewirtz et al., Science 242, 1303–1306 (1988)). 2×10$^5$ A"T"MNC or CD34$^+$ MNC were incubated in 5 ml polypropylene tubes (Fisher Scientific, Pittsburgh, Pa.) in a total volume of 0.4 ml of Iscove's modified Dulbecco's medium (IMDM) containing 2% human AB serum and 10 mM Hepes buffer. Oligomers were added at time zero (2.5–100 μg/ml), and 50% of the initial dose was added again 18 hours later (final total concentration –0.6–26 μM). Twenty-four hours after the first addition of oligomers, cells were prepared for plating in plasma clot or methylcellulose cultures. Cells (1×10$^5$ A"T"MNC or 1×10$^4$ CD34+NNC per dish) were not washed before plating. Control cultures were manipulated in an identical manner but were not treated with oligomers.

Colony Assays: Assays for hematopoietic progenitor cells of varying lineages were carried out essentially as reported (Id.). In brief, cells (10$^5$ A"T"MNC or 5×10$^3$ CD34$^+$ MNC) were resuspended in IMDM supplemented with 30% human AB serum, 1% BSA, 10$^{-4}$ M mercaptoethanol, and 10% citrated bovine plasma (Hyclone Laboratories, Denver, Colo.). Addition of the appropriate recombinant human growth factors allowed for stimulation of the following cell types:

CFU-E: 5 U/ml EPO;
BFU-E: 20 U/ml IL-3 and 5 U/ml EPO, or 100 ng/ml SCF and 5 U/ml EPO;
CFU-GM: 20 U/ml IL-3 and 5 ng/ml granulocyte-macrophage colony stimulating factor;
CFU-MEG: 20 U/ml IL-3 and 100 ng/ml IL-6.

One ml volumes were cultured in 35 mm petri dishes at 37° C., 5% CO$_2$, and 95% humidity. CFU-E colonies were scored at day 7, BFU-E colonies at day 14, CFU-MEG at day 12, and CFU-GM at day 11 of incubation. Colony identification was carried out as previously described (Id.).

Statistics: Statistical significance of differences between means of test groups was assessed by Mann-Whitney non-parametric analysis using a statistical software package (Statview 512+, BrainPower, Inc., Calabasas, Calif.). The results appear in Tables 1 and 2. Values presented are actual colonies counted, pooled from two or three individual studies.

TABLE 1

Effect of c-kit on A$^-$T$^-$ cell derived colony formation

| Progenitor Cell Type | Control | Sense | Scrambled Sequence | Antisense |
|---|---|---|---|---|
| CFU-E | 182, 209 | 153, 142 | 119, 128 | 33, 59 |
| | 1943, 543 | 1635, 1135 | 627, 649 | 243, 213 |
| | 148, 100 | 129, 176 | 149, 206 | 97, 107 |
| | Mean (±SE) = 522 ± 291 | Mean (±SE) = 562 ± 268 | Mean (±SE) = 313 ± 103 | Mean (±SE) = 125 ± 34 |
| BFU-E | 133, 152 | 117, 106 | 94, 64 | 60, 149 |
| | 534, 392 | 601, 249 | 273, 246 | 126, 113 |
| | 206, 172 | 215, 258 | 162, 246 | 59, 51 |
| | Mean (±SE) = 265 ± 66 | Mean (±SE) = 258 ± 74 | Mean (±SE) = 181 ± 36 | Mean (±SE) = 76 ± 14 |
| CFU-GM | 212, 189 | 231, 179 | 282, 193 | 195, 220 |
| | 412, 408 | 395, 421 | 457, 384 | 407, 471 |
| | 217, 241 | 239, 237 | 201, 199 | 293, 187 |
| | 209, 246 | Mean (±SE) = 282 ± 41 | Mean (±SE) = 286 ± 46 | Mean (±SE) = 296 ± 49 |
| | Mean (±SE) = 280 ± 42 | | | |
| CFU-MEG | 114, 107 | 133, 117 | 154, 113 | 127, 112 |
| | 93, 100 | 58, 52 | 53, 40 | 47, 54 |
| | Mean (±SE) = 104 ± 5 | Mean (±SE) = 90 ± 20 | Mean (±SE) = 90 ± 27 | Mean (±SE) = 85 ± 20 |

TABLE 2

Effect of c-kit oligomers on CD34$^+$ dell derived colony formation

| Progenitor Cell Type | Control | Sense | Scrambled Sequence | Antisense |
|---|---|---|---|---|
| CFU-E | 5, 9 | 16, 14 | 6, 21 | 1, 0 |
| | 16, 14 | 11, 17 | 22, 8 | 0, 0 |
| | 71, 79 | 78, 48 | 86, 91 | 40, 22 |
| | Mean (±SE) = 32 ± 12 | Mean (±SE) = 31 ± 11 | Mean (±SE) = 39 ± 15 | Mean (±SE) = 11 ± 7 |
| BFU-E | 179, 229 | 293, 120 | 191, 261 | 81, 75 |
| | 276, 281 | 241, 151 | 227, 283 | 34, 91 |
| | 271, 451 | 440, 361 | 321, 351 | 92, 111 |
| | Mean (±SE) = 281 ± 37 | Mean (±SE) = 286 ± 50 | Mean (±SE) = 272 ± 24 | Mean (±SE) = 81 ± 11 |
| CFU-GM | 321, 299 | 287, 360 | 321, 339 | 354, 319 |
| | 309, 312 | 316, 262 | 289, 324 | 349, 271 |
| | 114, 121 | 109, 103 | 84, 106 | 94, 103 |
| | 90, 135 | Mean (±SE) = 240 ± 44 | Mean (±SE) = 244 ± 48 | Mean (±SE) = 248 ± 49 |
| | Mean (±SE) = 213 ± 37 | | | |

As shown in Table 1, when A"T"MNC were employed as indicator cells, c-kit antisense oligomers inhibited growth of CFU-E –75%, and BFU-E –71%, when employed at the highest doses. Inhibition was sequence-specific since neither sense, nor scrambled sequence oligomers, significantly affected colony growth in comparison to untreated controls. In contrast to these results, CFU-GM and CFU-MEG derived colony formation was unaffected by exposure to any of the oligomers, at any of the doses employed (Table 1).

Similar results were obtained after exposure of CD34$^+$ cells to c-kit oligomers. As shown in Table 2, the mean number of CFU-E colonies decreased by –66% after exposure to c-kit antisense oligomers while the number of BFU-E colonies decreased –71%. Neither sense nor scrambled sequence oligomers inhibited colony formation. As was also noted with the less purified cell preparation, neither antisense nor control oligomers inhibited CFU-GM colony formation. The failure of c-kit antisense to inhibit CFU-GM and CFU-MEG is surprising since W/W$^v$ mice have been reported to have defective granulopoiesis and megakaryocytopoiesis (Chervenick et al., *Proc. Soc. Exp. Biol. Med.* 152, 398–402 (1976)).

Figure 3:
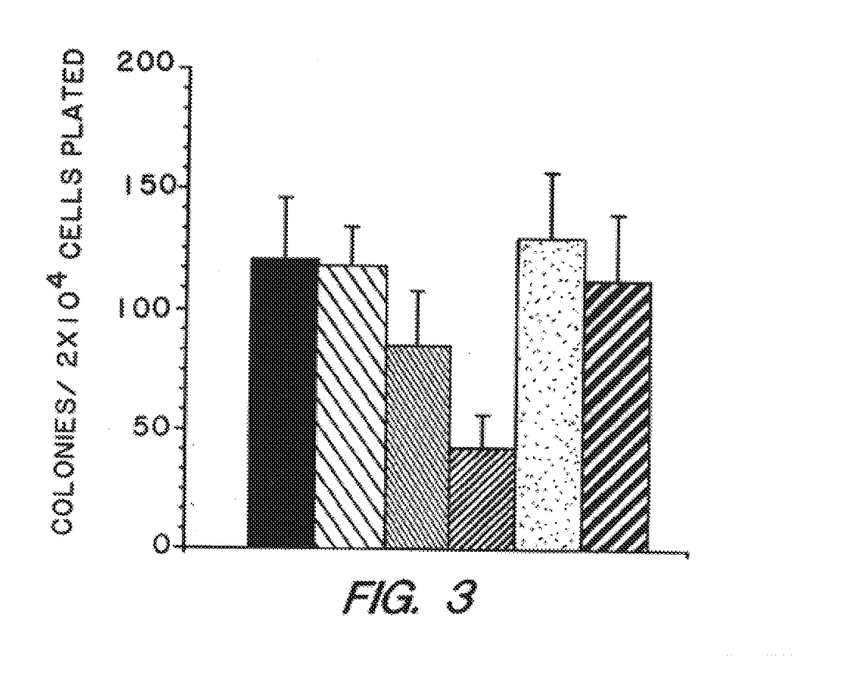
FIG. 3 shows the effect of c-kit oligodeoxyynucleotides on BFU-E-derived colony formation. Oligomers were added to cultures at time zero, and 50% of the initial dose was again added 18 hours later. The bars on the graph indicate: 1, untreated control cells; 2, antisense treatment of 20 μg/ml followed by 10 μg/ml; 3, antisense treatment of 40 μg/ml followed by 20 μg/ml; 4, antisense treatment of 100 μg/ml followed by 50 μg/ml; 5, sense treatment of 100 μg/ml followed by 50 μg/ml; 6, scrambled-sequence treatment of 100 μg/ml followed by 50 μg/ml.

Erythroid colony formation was inhibited in a dose-dependent fashion. See FIG. 3, showing the effect of various concentrations of c-kit antisense oligomer on BFU-E-derived colony formation. Moreover, residual colonies were much smaller for the antisense-treated cells veesus untreated controls (data not shown).

Reverse Transcription-Polymerase Chain Reaction (RT-PCR): As additional proof that the antisense effect was due to a specific decrement in c-kit mRNA levels, the kinetics of c-kit message expression in marrow mononuclear cells were examined, and the effect of oligomer exposure on c-kit mRNA levels was then assessed by the following RT-PCR procedure.

Total RNA was extracted from cells using the quanidine isothiocyante method of Chirgwin et al., *Biochemistry*, 18, 5294 (1979). Cells (2–5×10$^6$) were lysed in 250 μl of guanidine thiocyanate buffer (4M guanidine thiocyanate; 50 mM sodium acetate pH 5.0; 1 mM EDTA; IM β-mercaptoethanol; 0.5% sarcosyl) and then layered over 250 μl of a cesium chloride (5.7 M) cushion in Beckman open-top ultra clear centrifuge tubes (0.8 ml). Tubes were centrifuged (Beckman TL-100 Ultracentrifuge; 100,000 RMP; 1.5 hours; 20° C.) and the resulting RNA pellet was resuspended in –400 μl of water, precipitated with 0.3 M potassium acetate, washed twice in 75% ethanol, and then stored at –70° C. until used.

RNA was reverse-transcribed with 500 U of Moloney murine leukemia virus reverse transcriptase (MOMLV-RT) and 50 pmol of a 22-nucleotide oligodeoxynucleotide 3' primer complementary to nucleotides 1201–1179 (CTAGG-AATGT GTAAGTGCCT CC, SEQ ID NO:16) of the published c-kit CDNA sequence. The resulting CDNA fragment was amplified using 5 U of *Thermus acuaticus* (Taq) polymerase and a 22-nucleotide oligodeoxynucleotide 5' primer specific for c-kit nucleotides 842–864 (GGTTGACTAT CAGTTCAGCG AG, SEQ ID NO:17). Twenty-five μl of amplified product was electrophoresed on 4% agarose gel and subsequently transferred to a nylon filter. Filters were pre-hybridized, and then probed with a $^{32}$p end-labeled oligonucleotide probe (Caracciolo et al., *Science* 245, 1107–1109 (1989)) corresponding to the 21-nucleotide c-kit sequence (GATCCACTGC TGGTGTTCAG G, SEQ ID NO:18) contained within the amplified region (nucleotides 1068–1047). Autoradiography was performed by exposing filters on Kodak X-ray film at –70° C. using intensifying screens.

Figure 1:
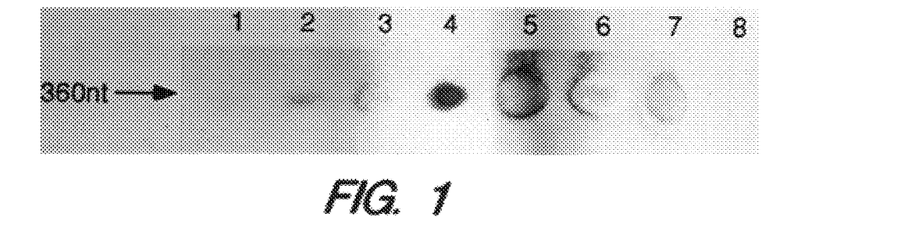
FIG. 1 is an autoradiograph of a reverse transcription-polymerase chain recaction gel indicating the increase in c-kit mRNA at intervals following stimulation of adherent, T lymphocyte-depleted human bone marrow cells (A"T"MNC) with 20 U/ml interleukin-3 and 5 U/ml erythropoietin: Lane 1 (t=0); lane 2 (2 hrs); lane 3 (8 hrs); lane 4 (12 hrs); lane 5 (24 hrs); lane 6 (36 hrs); lane 7 (48 hrs); lane 8 ($H_2O$ control).

A"T"MNC cells were kept for 24 hours at 4° C. in IMDM containing 2% human AB serum, then shifted to 37° C. and stimulated with IL-3 (20 U/ml) and EPO (5 U/ml) in 5% human AB serum. C-kit expression was determined at intervals according to RT-PCR. The results are indicated in FIG. 1. The FIG. 1 lanes indicate relative c-kit transcript amounts determined by autoradiography of RT-PCR hybridization gels at the following intervals after stimulation:

| FIG. 1 Lane | Time to RT-PCR Assay (hrs) |
|---|---|
| 1 | 0 |
| 2 | 2 |
| 3 | 8 |
| 4 | 12 |
| 5 | 24 |
| 6 | 36 |
| 7 | 48 |
| 9 | H$_2$O |

Lane 8 contained H$_2$O as a control. Expression appeared to peak at ~36 hours.

Figure 2:
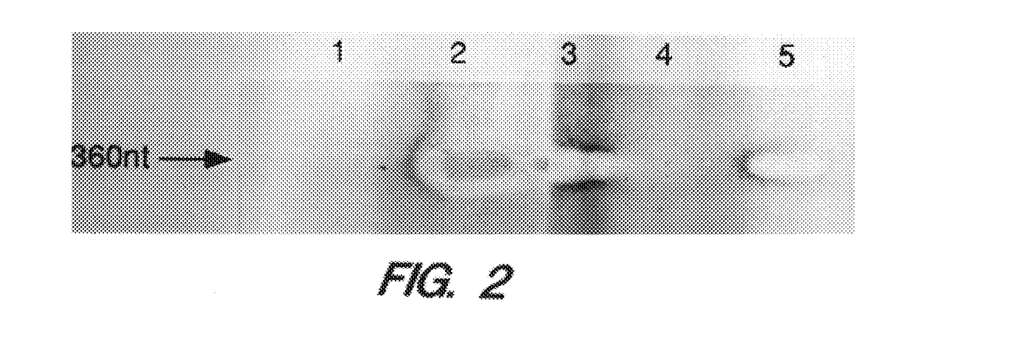
FIG. 2 is a similar autoradiograph indicating the effect of c-kit oligomer exposure on c-kit mRNA levels in A"T"MNC after stimulation by interleukin-3 and erythropoietin in 5% AB serum. Lane 1 (no oligomer, t=0); lane 2 (no oligomer, t=36 hrs); lane 3 (sense oligomer, 36 hrs); lane 4 (antisense, 36 hrs); lane 5 (scrambled sequence with identical base content, 36 hrs).

A"T"MNC cells stimulated (t=0) in the same manner were exposed to c-kit sense, antisense or mismatch oligomers. c-kit expression was assayed by RT-PCR (t=36 hrs) as above. The results appear in FIG. 2. The lanes are identified as follows:

| FIG. 2 Lane | Treatment |
|---|---|
| 1 | control cells (t = 0) |
| 2 | control cells (t = 36 hrs) |
| 3 | sense (t = 36 hrs) |
| 4 | antisense (t = 36 hrs) |
| 5 | mismatch (t = 36 hrs) |

Antisense-treated cells (lane 4) had no detectable c-kit mRNA, while sense (lane 3) and scrambled sequence (lane 5) treated cells had levels which were similar to those observed in untreated control cells at the same time point (lane 2).

EXAMPLE 2

Effect of c-kit Antisense Oligomer Exposure on Malignant Hematopoietic Progenitor Cell Growth To explore the importance of the c-kit receptor in regulating malignant hematopoietic cell growth, we employed a strategy which we have successfully employed in the past (Calabretta et al., *Proc. Nat. Acad. Sci. USA*, 88, 2351 (1991)), and which is essentially identical to that described above. A"T"MNC were obtained from patients with a variety of hematologic malignancies and exposed to the c-kit oligomers utilized in the preceding normal cell studies. Effects on the ability of malignant CFU-GM to form colonies, an index of the effect on malignant cell survival and proliferative activity, was then assessed. A total of twenty-two patients were studied, three with acute lymphocytic leukemia, four with acute myelogenous leukemia, ten with chronic myelogenous leukemia, and one with a myelodysplastic (pre-leukemic) syndrome and four with polycythemia vera. Overall response rates, and response rate by disease type, is given in Table 3.

TABLE 3

Effect of c-kit oligomers on growth of malignant hematopoietic colony forming cells

| Disease Type | No. Pts | Responders | % Decrease Colonies | Non-Responders |
|---|---|---|---|---|
| Acute lymphocytic leukemia | 3 | 1 | 68% | 2 |
| Acute myelogenous leukemia | 4 | 1 | 63% | 3 |

TABLE 3-continued

Effect of c-kit oligomers on growth of malignant hematopoietic colony forming cells

| Disease Type | No. Pts | Responders | % Decrease Colonies | Non-Responders |
|---|---|---|---|---|
| Chronic myelogenous leukemia | 10 | 5 | 84% <br> 33% <br> 40% <br> 90% <br> 78% <br> Mean = 65% ± 26% | 5 |
| Myelodysplastic syndrome | 1 | 1 | 68% | — |
| Polycythemia vera | 4 | 4 | Mean 74% ± 24% | — |
| TOTAL | 22 | 12 | 66% | 10 |

While the number of patients in categories other than CML is small, the data nonetheless suggest that patients with CML are particularly likely to respond to c-kit antisense. Accordingly, c-kit antisense oligomers are believed particularly useful as CML bone marrow purging agents. In addition, because of their marked inhibition of erythroid progenitor cells, it is believed that c-kit oligomers are useful in controlling the markedly elevated hemoglobin/hematocrit found in patients with PV, another myeloproliferative disorder.

EXAMPLE 3

Effect of c-kit Antisense Olipomer Exposure on BFU-E Responsiveness to Stem Cell Factor To provide proof that c-kit antisense mediated inhibition of erythropoiesis was due to the absense of KIT receptor function, we sought to demonstrate that BFU-E responsiveness to stem cell factor (SCF) could be abolished in a sequence-specified manner after exposure to c-kit oligomers. Accordingly, CD34 +MNC ($2 \times 10^4$) were cloned in the presence of 5 units of EPO and 100 ng of SCF per ml alone or with sense, antisense, or scrambled-sequence c-kit oligomers (final concentration, 150 µg/ml (~26 µM)). In four experiments, 191±19 BFU-E (mean±SD) were grown in the presence of the growth factors alone. These numbers were not statistically different from those cloned with sense (183±29; P=0.654) or scrambled-sequence oligomers (180±20; P=0.758). In the presence of the c-kit antisense oligomers, BFU-E-derived colony formation was completely abolished (0.4±0.7; P<0.0001), suggesting that KIT receptor was no longer present to interact with its ligand.

The following non-limiting example illustrates one methodology for bone marrow purging according to the present invention.

EXAMPLE 4

Bone Marrow Purging with c-kit Antisense Oligonucleotide

Bone marrow is harvested from the iliac bones of a donor under general anesthesia in an operating room using standard techniques. Multiple aspirations are taken into heparinized syringes. Sufficient marrow is withdrawn so that the marrow recipient will be able to receive about $4 \times 10^8$ to about $8 \times 10^8$ processed marrow cells per kg of body weight. Thus, about 750 to 1000 ml of marrow is withdrawn. The aspirated marrow is transferred immediately into a transport medium (TC-199, Gibco, Grand Island, N.Y.) containing 10,000 units of preservative-free heparin per 100 ml of medium. The aspirated marrow is filtered through three progressively finer meshes until a single cell suspension results, i.e., a suspension devoid of cellular aggregates, debris and bone particles. The filtered marrow is then processed further into an automated cell separator (e.g., Cobe 2991 Cell Processor) which prepares a "buffy coat": product, (i.e., leukocytes devoid of red cells and platelets). The buffy coat preparation is then placed in a transfer pack for further processing and storage. It may be stored until purging in liquid nitrogen using standard procedures. Alternatively, purging can be carried out immediately, then the purged marrow may be stored frozen in liquid nitrogen until it is ready for transplantation.

The purging procedure may be carried out as follows. Cells in the buffy coat preparation are adjusted to a cell concentration of about $2 \times 10^7$/ml in TC-199 containing about 20% autologous plasma. C-kit anti-sense oligodeoxynucleotide, for example, in a concentration of about 8 mg/ml, is added to the transfer packs containing the cell suspension. Recombinant human hematopoietic growth factors, e.g., rH IL-3 or rH GM-CSF, may be added to the suspension to stimulate growth of hematopoietic neoplasms and thereby increase their sensitivity c-kit antisense oligonucleotide toxicity. The transfer packs are then placed in a 37° C. waterbath and incubated for 18–24 hours with gentle shaking. The cells may then either be frozen in liquid nitrogen or washed once at 4° C. in TC-199 containing about 20% autologous plasma to remove unincorporated oligomer. Washed cells are then infused into the recipient. Care must be taken to work under sterile conditions wherever possible and to maintain scrupulous aseptic techniques at all times.

The present invention may be embodied in other specific forms without departing from the spirit or essential attributes thereof and, accordingly, reference should be made to the appended claims, rather than to the foregoing specification, as indicating the scope of the invention.

All references cited herein with respect to synthetic, preparative and analytical procedures are incorporated herein by reference.

We claim:

1. A 15 ml to 30 ml oligonucleotide which has a nucleotide sequence selected from the group of sequences consisting of:
    SEQ ID NO:2,
    SEQ ID NO:3,
    SEQ ID NO:4,
    SEQ ID NO:5,
    SEQ ID NO:6,
    SEQ ID NO:7,
    SEQ ID NO:8,
    SEQ ID NO:9,
    SEQ ID NO:10,
    SEQ ID NO:11,
    SEQ ID NO:12, and
    SEQ ID NO: 13.

2. An oligodeoxynucleotide according to claim 1 having the nucleotide sequence SEQ ID NO:10.

3. A pharmaceutical composition comprising a pharmaceutical carrier and a 15 ml to 30 ml oligonucleotide which has a nucleotide sequence selected from the group of sequences consisting of:

SEQ ID NO:2,
SEQ ID NO:3,
SEQ ID NO:4,
SEQ ID NO:5,
SEQ ID NO:6,
SEQ ID NO:7,
SEQ ID NO:8,
SEQ ID NO:9,
SEQ IDNO:10,
SEQ ID NO:11,
SEQ ID NO:12, and
SEQ ID NO:13.

4. A composition according to claim 3 wherein the oligodeoxynucleotide has a nucleotide sequence of SEQ ID NO:10.

5. A method oftreating bone marrow from an individual with a hematologic neoplasm comprising incubating said bone marrow cells in vitro with an amount of an about 12-mer to about 40-mer antisense oligonucleotide comprised of a region complementary to the translation initiation region of the c-kit mRNA, said amount effective to cause an inhibition of about at least 33% in colony formation when compared to untreated bone marrow of the same individual.

6. An oligonucleotide consisting of an about 12-mer to about 40-mer antisense oligonucleotide comprised of a region complementary to the translation initiation region of the c-kit MRNA.

7. A pharmaceutical composition comprising about a 12-mer to about 40-mer antisense oligonucleotide comprised of a region complementary to the translation initiation region of the c-kit mRNA and a pharmaceutically acceptable carrier.

* * * * *